United States Patent [19]

Schlatter et al.

[11] 3,997,553

[45] * Dec. 14, 1976

[54] 2-BENZIMIDAZOLECARBAMIC ACID ESTERS BY THE CYANAMIDE PROCESS

[75] Inventors: Rudolph Schlatter, Chadds Ford, Pa.; Charles DeWitt Adams, Wilmington, Del.

[73] Assignee: E. I. Du Pont de Nemours and Company, Wilmington, Del.

[*] Notice: The portion of the term of this patent subsequent to Sept. 16, 1992, has been disclaimed.

[22] Filed: Jan. 15, 1975

[21] Appl. No.: 541,241

Related U.S. Application Data

[63] Continuation of Ser. No. 836,580, June 25, 1969, Pat. No. 3,905,991, which is a continuation-in-part of Ser. No. 745,403, July 17, 1968, abandoned, which is a continuation-in-part of Ser. No. 674,739, Oct. 12, 1967, abandoned, which is a continuation-in-part of Ser. No. 594,384, Nov. 15, 1966, abandoned.

[52] U.S. Cl. .......................................... 260/309.2
[51] Int. Cl.$^2$ ..................................... C07D 235/32
[58] Field of Search ................................ 260/309.2

[56] References Cited

UNITED STATES PATENTS

| | | | |
|---|---|---|---|
| 3,147,274 | 9/1964 | Moyle et al. | 260/309.2 |
| 3,255,202 | 6/1966 | Johnson | 260/309.2 |

FOREIGN PATENTS OR APPLICATIONS

| | | | |
|---|---|---|---|
| 666,795 | 1/1966 | Belgium | 260/309.2 |

OTHER PUBLICATIONS

Derwent Pharmaceutical Documentation Specification Book No. 463 Feb. 4, 1966 19,779–19,841 pp. 239–243 (Derwent Basic No. 19830).
Hofmann Imidazole and its Derivatives Part I pp. 260–267. N.Y., Interscience, 1953.
Pierron Comptes Rendus vol. 151, pp. 1364–1366 (1910).

*Primary Examiner*—Natalie Trousof

[57] ABSTRACT

A process for making 2-benzimidazolecarbamic acid, alkyl esters by reacting cyanamide or a cyanamide salt with an alkyl chloroformate in a weakly acidic to basic medium at a temperature between 0° and 105° C. to form an alkyl cyanocarbamate salt; then reacting the alkyl cyanocarbamate salt with an o-phenylenediamine in an acidic medium at a temperature between 40° and 130° C. to form the desired product and recovering it from the reaction mixture.

The 2-benzimidazolecarbamic acid, alkyl esters are useful as fungicides and also useful as intermediates in the preparation of dialkyl esters of 2-carboxyaminobenzimidazole-1-carboxylic acids.

14 Claims, No Drawings

2-BENZIMIDAZOLECARBAMIC ACID ESTERS BY THE CYANAMIDE PROCESS

CROSS-REFERENCE TO RELATED APPLICATIONS

This application is a continuation of our copending application Ser. No. 836,580, filed June 25, 1969 now U.S. 3,905,991, which is a continuation-in-part of our copending application Ser. No. 745,403, filed July 17, 1968 now abandoned, which application is a continuation-in-part of our copending application Ser. No. 674,739, filed Oct. 12, 1967 now abandoned, which application is a continuation-in-part of our then copending application Ser. No. 594,384, filed Nov. 15, 1966, now abandoned.

BRIEF SUMMARY OF THE INVENTION

This invention relates to novel processes for the manufacture of alkyl esters of certain benzimidazolecarbamic acids. More particularly, this invention relates to processes for the manufacture of such esters from cyanamide or cyanamide salts.

Alkyl esters of 2-benzimidazolecarbamic acids represented by the formula:

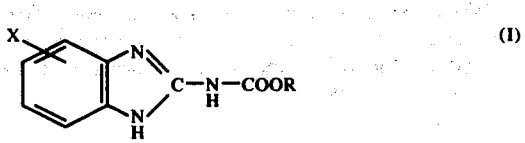

where

R is alkyl of 1 through 4 carbon atoms; and

X is hydrogen, halogen, nitro or alkyl of 1 through 4 carbon atoms; are useful as fungicides. The compounds when X is hydrogen and R is alkyl of 1 to 4 carbon atoms are particularly useful. The above compounds are also useful as intermediates in the preparation of dialkyl esters of 1-carboxy-2-benzimidazolecarbamic acids represented by the formula:

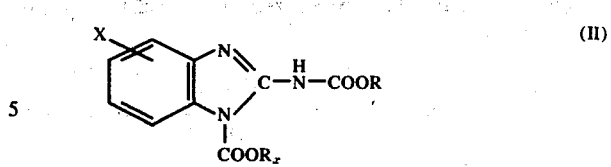

where

X is defined in formula (I) above and

R and $R_x$ are the same or different and are alkyl of 1 through 4 carbon atoms.

These compounds are disclosed in U.S. Pat. No. 2,933,504 and are very useful as fungicides.

U.S. Pat. No. 3,010,968 describes a process for making the 2-benzimidazolecarbamic acid esters of formula (I) by reacting thiourea with dimethyl sulfate to produce 2-methylthiopseudourea sulfate. This reaction product is then reacted with an alkyl chloroformate and a base to produce an acylated 2-methylthiopseudourea, which is then reacted further with an o-phenylenediamine in the presence of a protonic acid to produce the desired product.

The process of this invention has several advantages over the process set forth in the above patent. One particular advantage is that commercially available, inexpensive, technical-grade cyanamide salts or cyanamide solutions can be used instead of the relatively more expensive thiourea materials. Further, the process of this invention does not require the handling or disposal of obnoxious methyl mercaptan materials which are by-products of the art process. Additionally, the process of this invention can be conducted in a batch or continuous manner with normal reaction vessels.

The process of this invention can be summarized by the following equations when a cyanamide salt and water as a solvent are employed:

(Step 1)

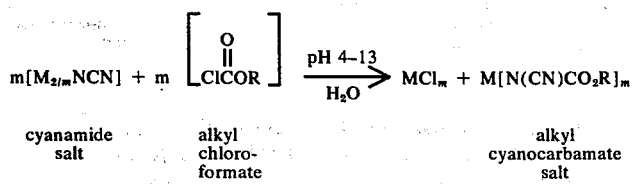

(Step 2 — condensed equation form)

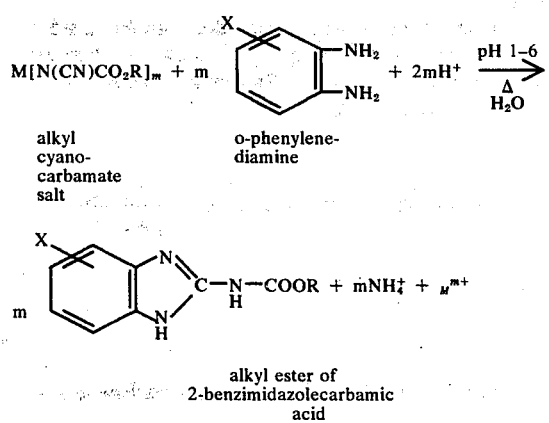

Step 2 above can be represented in more detail by the following equations:

(a)
$$M[N(CN)CO_2R]_m + mH^+ \xrightarrow[pH\ 1-6]{H_2O} m\ HN(CN)CO_2R + M^{m+}$$

alkyl cyanocar-        alkyl cyanocarbamate
bamate salt (b)

$$m\ \underset{}{\text{(X-substituted benzene-1,2-diamine)}} + mHN(CN)CO_2R + mH^+ \xrightarrow[pH\ 1-6]{H_2O}$$

$$m\ \underset{}{\text{(X-substituted benzimidazole)}}\!\!-\!C\!-\!NHCO_2R + mNH_4^+$$

alkyl ester of
2-benzimidazolecarbamic acid where
R is alkyl of 1 through 4 carbon atoms; and
X is hydrogen, halogen, nitro or alkyl of 1 through 4 carbon atoms;
M is an alkali metal or an alkaline earth metal; and
m is the valence of M, and
H$^+$ may be derived from any acid.

In Step 1 above, when a cyanamide salt is employed, the cyanamide is present in the solution in anion form. However, cyanamide can also be used in Step 1 if a base is added to the solution to maintain the desired pH. Step 1 in this embodiment is illustrated by the following equation when water is employed as solvent:

$$mH_2NCN + mCl\!-\!\overset{O}{\underset{\|}{C}}\!-\!OR + 2M(OH)_m \xrightarrow[pH\ 4-13]{H_2O} M[N(CN)CO_2R]_m + MCl_m + 2mH_2O$$

cyana-   alkyl       base                        alkyl
mide    chloro-                                cyanocarbamate
        formate                             salt In this reaction the base used is not critical. All that is necessary is that it be able to take up the HCL generated and thereby maintain the reaction mass weakly acidic to basic. Thus, for example, any basic alkali metal or alkaline earth metal compound can be used as the base. Alkali metal and alkaline earth metal hydroxides are preferred, although oxides and carbonates can be used.

Quaternary ammonium hydroxides can be used as base when cyanamide is employed. Step 1 in this embodiment is illustrated by the following equation when water is employeed as solvent.

$$H_2NCN + Cl\overset{O}{\underset{\|}{C}}OR + 2[NR_1R_2R_3R_4]\cdot OH \xrightarrow[pH\ 4-13]{H_2O}$$

cyana-   alkyl       base
mide    chloro-
        formate where
R$_1$, R$_2$, and R$_3$ are alkyl of 1 through 4 carbon atoms; and R$_4$ is either alkyl of 1 through 4 carbon atoms or aralkyl of 7 through 12 carbon atoms.

The cheaper and more readily available quaternary ammonium hydroxides, such as tetramethylammonium hydroxide or benzyltrimethylammonium hydroxide, are preferred.

Tertiary amines can also be used as bases when cyanamide is employed. Step 1 in this embodiment is illustrated by the following equation when water is employed as solvent:

$$H_2NCN + Cl\overset{O}{\underset{\|}{C}}OR + 2NR_5R_6R_7 \xrightarrow[pH\ 4-13]{H_2O}$$

cyana-   alkyl       amine
mide    chloro-    base
        formate $$[HNR_5R_6R_7]\cdot[N(CN)CO_2R] + [HNR_5R_6R_7]\cdot Cl$$

alkyl cyanocarbamate salt where
R$_5$ and R$_6$ are alkyl of 1 through 4 carbon atoms; and
R$_7$ is alkyl of 1 through 4 carbon atoms, or aralkyl of 7 through 12 carbon atoms.

Tertiary amines such as trimethylamine and triethylamine are preferred.

Certain other substituted tertiary amines, such as triethanolamine and triethylenediamine, can be used as bases when cyanamide is employed. Step 1 in this embodiment is illustrated by the following equation when water is employed as solvent:

$$H_2NCN + Cl\overset{O}{\underset{\|}{C}}OR + 2N(R_8)_3 \xrightarrow[pH\ 4-13]{H_2O}$$

cyana-   alkyl       amine
mide    chloro-    base
        formate

-continued

[HN(R$_8$)$_3$] . [N(CN)CO$_2$R] + [HN(R$_8$)$_3$] . Cl alkyl cyanocarbamate salt where
N(R$_8$)$_3$ is triethanolamine or triethylenediamine.

The above equations for steps 1 and 2 have all been directed to reactions conducted in water. However, the use of water, although preferred, is not critical; any suitable solvent can be used. Other solvents which could be used are the lower alkanols, acetone, dioxane, ethylene glycol, and the like, and mixtures of water with miscible co-solvents. Preferably the solvent is water or mixtures of water with lower alcohols. Since it is convenient to use the same solvent in both step 1 and step 2, the solvent used should also be compatable with the acid used in step 2.

The operation of Step 1 of this process thus produces solutions which contain salts of alkyl cyanocarbamates. In order to begin the operation of Step 2, acids are added to these solutions. This acidification converts the salts to the corresponding alkyl cyanocarbamates. These reactions are illustrated by the following equations wherein water is used as the solvent:

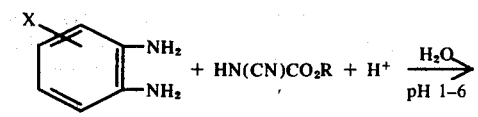

o-phenylenediamine    alkyl cyano-
                      carbamate

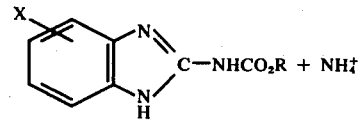

alkyl ester of
2-benzimidazolecarbamic acid

Thus, two reactions occur during the operation of Step 2. The first reaction is the acidification of the salt of the alkyl cyanocarbamate in order to furnish the alkyl cyanocarbamate. The second reaction is between the alkyl cyanocarbamate and o-phenylenediamine or substituted o-phenylenediamine to furnish the 2-benzimidazolecarbamic acid, alkyl ester. These reactions can be represented by either one combined equation or by two separate equations.

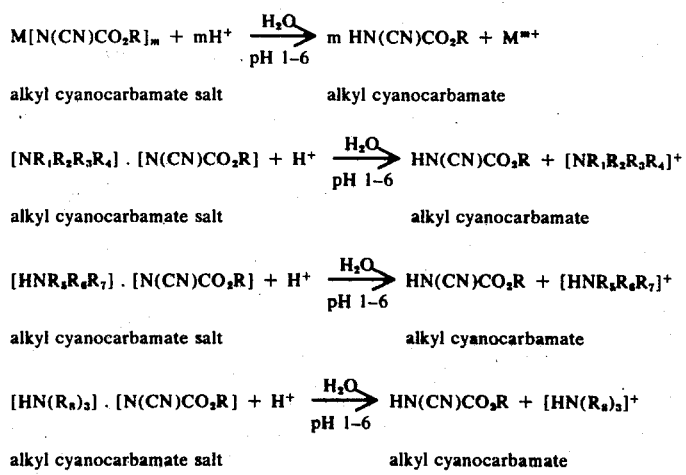

When o-phenylenediamine or substituted o-phenylenediamines are added to the acidified solutions of alkyl cyanocarbamates and the resulting mixtures are heated or stored under acidic conditions, the alkyl cyanocarbamates react with o-phenylenediamine or substituted o-phenylenediamines to give 2-benzimidazolecarbamic acid, alkyl esters. These reactions are illustrated by the following equation when water is used as solvent:

A second outcome can be obtained if the mixture which contains an alkyl cyanocarbamate and o-phenylenediamine or a substituted o-phenylenediamine is not heated or stored. If the mixture is filtered soon, an insoluble salt of an alkyl cyanocarbamate with o-phenylenediamine or a substituted o-phenylenediamine can be recovered. These salts are novel compounds and represent another aspect of the present invention. They are represented by the following formula:

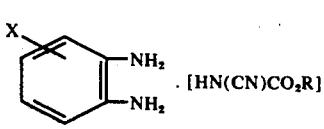

alkyl cyanocarbamate salt with o-phenylenediamine.

The 2-benzimidazolecarbamic alkyl esters produced by the processes above can be converted to the esters shown in Formula II. This conversion reaction is summarized by the following equation:

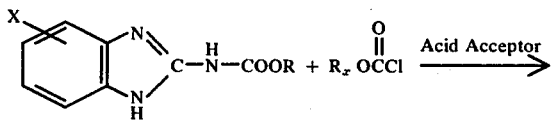 + 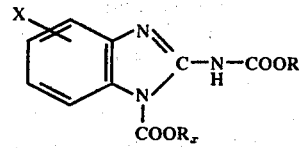

wherein

X, R and $R_x$ are as defined previously.

In another aspect this invention is related to the novel compounds methyl cyanocarbamate and salts of methyl cyanocarbamate.

DETAILED DESCRIPTION OF THE INVENTION

In the first step of the process of the invention, the appropriate alkyl chloroformate is reacted with a cyanamide source, i.e., either cyanamide or a salt of cyanamide, in weakly acidic to basic solvent media to form a salt of an alkyl cyanocarbamate. The cyanamide salt is not critical, all that is necessary is that it furnish cyanamide anions which are capable of reacting with an alkyl chloroformate. Thus readily available technical-grade salts can be used in this process. Suitable starting materials are cyanamide alkaline earth or alkali metal salts, particularly the salts with magnesium, potassium, sodium and calcium. Commercially available calcium cyanamide is a preferred starting material. Cyanamide itself or a solution of cyanamide in water are also preferred starting materials. When cyanamide is employed as starting material, the base used is not critical. All that is necessary is that it be able to neutralize the by-product hydrogen chloride which forms.

In the first step, when the alkyl chloroformate is reacted with a cyanamide salt, either a single salt, i.e., $M(HNCN)_m$ or a double salt, i.e., $M_{2/m}NCN$, can be used.

The first step is conducted in a suitable solvent. Solvents which can be used are water, lower alcohols, acetone, dioxane, and the like or mixtures of water with miscible cosolvents. Preferably the solvent is water or mixtures of water with lower alcohols.

The concentration of the starting materials in the reaction mixture are not critical; however, for economic reasons, high concentrations will usually be chosen. With respect to the slurry or solution of the cyanamide salts, the concentration is only limited by the handling characteristics of the slurry.

When a cyanamide salt is used, it is preferred to add, with mixing, the alkyl chloroformate to the slurry or solution containing the cyanamide salt. When cyanamide is used, the alkyl chloroformate and base can be added concurrently to a solution of cyanamide or the base can be added last. During this additon, preferably the molar quantity of base added at any point should be equivalent to the molar quantity of chloroformate.

During the first step it is important to maintain the reaction mass in a weakly acidic to basic condition. When water or mixtures of water with miscible co-solvents are used, the pH should be maintained within the range of 4 to 13. As previously mentioned, when free cyanamide is used, this pH range can be maintained by adding base as required. When cyanamide is used, the preferred range of pH is from 6 to 9. The most preferred range of pH is from 6 to 8. However, with cyanamide salts, it is preferred to maintain the pH range between 8 and 12.

The temperature of this first step of the process is not critical within the range of 0° to 105° C. If desired, this step can be conducted at higher temperatures under pressure; generally the range of 25° to 70° C. is preferable.

The reaction is rapid and the product is stable in the reaction medium; thus the time of reaction is not critical and the product can be used directly in the second step or held for a period of time, depending upon which is desirable from an equipment viewpoint. In general, the reaction time will depend upon heat transfer rate and can be from 5 minutes to 2 hours.

When technical grade cyanamide salts have been used in the first step, sometimes insoluble impurities and salts, e.g., calcium salts, are included in the reaction mixture. It is preferred to filter these impurities out prior to going forward into step 2.

In the second step of the process, o-phenylenediamine is added to the reaction product from step 1, or if cyanamide salts have been used, to the filtered reaction product. The o-phenylenediamine can be added to the reaction product while the product is at the temperature it was during the first step, 0° up to 105° C.

Optionally, the o-phenylenediamine can be in the form of a granular or flaked solid, as a solution in water or another solvent, as a melt, or as a mineral acid salt. When mineral acid salts are used, the amount of acid required to produce the desired pH will be reduced correspondingly.

Acid is then added in order to convert the salt of the alkyl cyanocarbamate to the alkyl cyanocarbamate. This order of addition, o-phenylenediamine followed by acid, is ordinarily the more convenient. However, the reverse order of addition, acid followed by o-phenylenediamine, gives satisfactory results when it is used.

To carry out the condensation and ring-closure involved, during the second reaction acid in addition to that needed to convert the alkyl cyanocarbamate salt to free alkyl cyanocarbamate is added so that the pH is maintained in the range of 1 to 6, preferably 2.5 to 5. The most preferred pH range is 3.5 to 4.5. The desired pH can be maintained by the addition of any acid, for example, formic acid, acetic acid, hydrochloric acid, sulfuric acid, phosphoric acid, hydroxyacetic acid, sulfamic acid, and the like.

The reason that additional acid is added during the ring-closure reaction of Step 2 is to neutralize the by-product ammonia which is formed. If acid is not added the ammonia will react with the alkyl cyanocarbamate in an acid-base reaction with the result that the alkyl cyanocarbamate is no longer available for reaction with the o-phenylenediamine. This undesired reaction of ammonia with an alkyl cyanocarbamate is shown by the following equation:

$$NH_3 + HN(CN)CO_2R \rightarrow [NH_4]\cdot[N(CN)CO_2R].$$

The ring-closure reaction is exothermic and it can be conveniently controlled when the rate of acid addition does not outpace the rate of ammonia production. Thus if the reaction becomes too vigorous, the acid addition can be stopped and the ring-closure reaction will slow as the ammonia concentration increases. Resuming the acid addition will cause the ringclosure reaction to proceed again. A convenient method of determining the optimum rate for acid addition is with a pH meter. Beside the fact that the ring-closure reaction is easier to control, the yields are somewhat higher when the acid is added in a controlled manner.

An alternate technique of acid addition which gives somewhat lower yields is to add all at once, or very rapidly, the theoretical amount of acid that is required to neutralize the by-product ammonia. In this event, the acid is already present in the solution and it reacts with the ammonia as soon as it appears. Some acid in excess of the theoretical amount can be tolerated as long as the pH does not drop below 1.0.

Although emf (electromotive force) measurement with a pH meter is perhaps the most convenient method of determining the acidity of the medium during the ring-closure reaction, it is not the only method which can be used. For example, acid-base indicators which change colors in certain pH ranges can be used.

A similar statement can be made about monitoring the progress of the reactions in Step 1. Although pH measurement with a pH meter is perhaps the most convenient method, acid-base indicators can also be used.

Those skilled in the art will realize that the pH values which are reported in the examples are in fact instrument readings which may have little or no relationship to the actual activities or concentrations of hydrogen ions in the solutions. It is very difficult as a practical matter to determine the actual hydrogen ion activities in such concentrated solutions. These pH values are, however, reproducible numbers which are extremely valuable for following the progress of the various reactions. This is because these pH values are defined operationally by the following equation.

$$\text{pH(measured)} = \text{pH}(S) + \frac{E - E_s}{(RT\ln 10)/F}$$

Where:
pH(measured) is the pH of the test solution;
pH(S) is the known pH of a reference standard solution;
E is the emf of the cell when in contact with the test solution;
$E_s$ is the emf of the cell when it is in contact with the reference standard solution;
T is temperature;
R is the gas constant; and
F is the Faraday.

R. G. Bates has written an informative discussion of this equation (Kirk-Othmer Encyclopedia of Chemical Technology, second completely revised edition, Vol. II, p. 380, Interscience Publishers, a division of John Wiley and Sons, Inc., New York, 1966).

The equation shows that the pH meter is responding to the difference in electromotive force (emf) which develops between a glass electrode and a reference electrode of constant potential when the electrodes are removed from the standard solution and place in contact with the test solution. For convenience, the pH meter converts the emf difference to a pH difference, but the progress of the reactions could be followed by emf readings instead, if a potentiometer were used in place of a pH meter.

The following procedure has been found to be effective for obtaining reproducible and useful pH readings. A pH meter in good working order is equipped with a glass electrode and either a mercury-mercurous chloride (calomel) or a silver-silver chloride electrode. The electrodes are placed in a reference standard solution, either pH 4.00 or 7.00, which has been prepared according to the recommendations of National Bureau of Standards Research Paper RP 1495. The temperature compensator of the meter is adjusted to the temperature of the standard solution, and the meter is adjusted to the pH of the standard solution with the standardization control. The electrodes are then transferred to the test solution in order to obtain an operational pH reading. If the temperature of the test solution is different from that of the reference standard solution, and it usually is, the temperature compensator on the meter must be adjusted accordingly.

The preferred pH ranges mentioned so far are potentiometrically determined pH values which pertain to those mediums which contain water, i.e., mediums where water is the solvent, water and a water-miscible liquid are the solvent, water is added along with one of the reagents as for example when 50% cynamide or 50% sodium hydroxide are used, or where water is formed as a reaction by-product in Step 1. However, it is well known that pH values which are obtained in a medium which contains water do not necessarily correspond to pH values which are obtained in an anhydrous medium. It is still possible though to obtain pH or emf values in anhydrous mediums which reflect changes in acid strength in the medium. This permits the monitoring of the reactions of this process by potentiometric methods. Thus, for each individual anhydrous medium it is possible to establish through experimentation the ranges of preferred emf or pH values for both steps of the process. These preferred values may or may not be the same as for mediums which contain water. Some examples of anhydrous mediums are the lower alcohols, acetone, dioxane, tetrahydrofuran, ethylene glycol, and the like.

The reaction between the alkyl cyanocarbamate and the o-phenylenediamine will occur at temperatures above 40° C.; at lower temperatures, the reaction is very slow. The reaction mixture should be maintained between 40° C. and reflux, preferably 60° to 105° C. This second step reaction can also be conducted under pressure if this is desired. If this is done, the temperature can go up to 130° C. or higher.

During the heating step, the desired product will precipitate. Thus the completion of precipitation is an indication that the reaction is complete. The time is not critical, and depends upon the temperature, concentration, and pH. Thus at a pH of 2.5 to 5 and a temperature between 70° and 105° C., the reaction time can be 5 to 180 minutes. When lower temperatures are used, the time will be longer, and if the pH is not maintained in the range of 1 – 6, the reaction will be very slow or not occur at all.

The desired product can then be recovered by any of the conventional means, for example, spray drying, filtration, or centrifuging, or it may be transferred to another liquid medium by distillation of the solvent.

In the overall process, the reactants can be used in the mole equivalent ratios indicated in the following table:

| REACTANTS | MOLE EQUIVALENTS | PREFERRED MOLE EQUIVALENTS |
|---|---|---|
| Cyanamide or cyanamide salts | 1 to 3 | 1 to 2.2 |
| alkyl chloroformate | 1 to 3 | 1 to 1.8 |
| o-phenylenediamine or derivatives thereof | 1 | 1 |

It should be understood that the molar equivalents are not critical at the upper limit; however, they will not be practical or economical at higher levels. It is obvious that the concentration in the second step will depend upon the concentration in the first.

It has also been found that the first step of this process has produced a novel compound, methyl cyanocarbamate. This compound can be prepared by reacting methyl chloroformate with a cyanamide salt and then acidifying the resulting solution, or reacting the methyl chloroformate with cyanamide in the presence of a base such as sodium hydroxide and then acidifying the resulting solution. This reaction is exemplified by the following equations when water is the solvent:

(a)
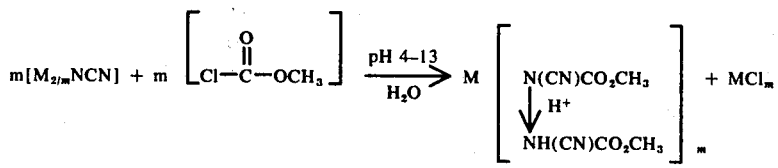

or (b)
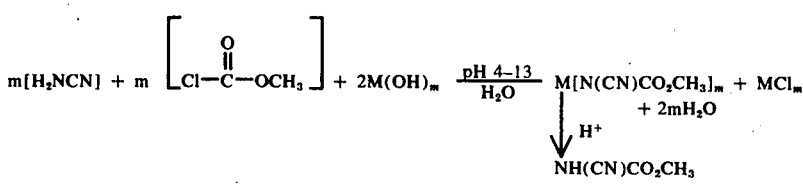

The methyl cyanocarbamate thus produced can be isolated by extraction with organic solvents if desired; however, the above solution containing the methyl cyanocarbamate can be used for the second step in the process of the invention. The product, methyl cyanocarbamate, is therefore a useful cmpound in that it can be reacted with o-phenylenediamine to form 2-benzimidazolecarbamic acid, methyl ester.

The various salts of methyl cyanocarbamate which are obtained in solution from the operation of the first step of this process are also novel compounds. The sodium and calcium salts of methyl cyanocarbamate can be isolated easily from the solutions since they precipitate upon cooling and are recoverable by filtration. The potassium and trimethylamine salts of methyl cyanocarbamate are too soluble in water be recovered in this way. They can be isolated in a dry state, if this is desired, by first isolating methyl cyanocarbamate and then treating it in an organic solvent with potassium methoxide or trimethylamine. These methyl cyanocarbamate salts, are set forth previously, are the intermediates formed in the first step of the process of the invention and are used in the second step of this process.

In order that the above aspects of the invention can be better understood, the following Examples are offered. Parts and percentages are by weight unless otherwise indicated.

EXAMPLE 1

Preparation of 2-benzimidazolecarbamic acid, methyl ester

Methyl chloroformate (75.6 parts) is added with good stirring to a slurry of 80 parts of technical grade calcium cyanamide and 300 parts of water. The temperature is maintained at 40° to 50° C. by ice-bath cooling. After stirring the reaction mixture for 1 hour, the mixture is filtered and the insolubles washed in portions with 100 parts of water.

To the combined wash and filtrate is added 43.2 parts of o-phenylenediamine. The pH of the mixture is adjusted to 3.5 with the addition of concentrated hydrochloric acid. The solution is then heated rapidly to 90° C. and the temperature maintained in the range of 90° to 98° C. for thirty minutes. During this time, the pH is maintained at 2.5 to 3.1 by the addition of concentrated hydrochloric acid.

The reaction mixture is then filtered and the solid washed with water and acetone, and then dried in a vacuum oven at 120° C. This results in a yield of 64 parts of 2-benzimidazolecarbamic acid, methyl ester, or a yield of 83.3% based on the o-phenylenediamine.

EXAMPLE 2

Preparation of 2-benzimidazolecarbamic acid, methyl ester

To a suitable reaction vessel are added 50.4 parts of a 50% cyanamide solution and 250 parts of water. Then 56.8 parts of methyl chloroformate and 88 parts of 50% sodium hydroxide are added simultaneously. The pH of this mixture is controlled at 8.0 to 8.5 by the rate of sodium hydroxide addition, and the temperature is maintained near 40° C. by ice-bath cooling.

The resulting solution is further reacted by addition of 54 parts of o-phenylenediamine. The mixture is brought to pH 3.5 with concentrated hydrochloric acid. The mixture is then heated rapidly to 90° C. and for thirty minutes the temperature is controlled at 91° to 97° C. During this time, the pH is maintained at 3.0 to 3.6 by the addition of concentrated hydrochloric acid. The resulting mixture is then cooled to 60° C. and filtered. The product is washed with water and acetone and dried in a vacuum oven at 130° C. This result in 78.9 pats of 2-benzimidazolecarbamic acid, methyl ester, or a yield of 82.6% based on the o-phenylenediamine.

EXAMPLE 3

Preparation of methyl cyanocarbamate

Into a suitable vessel fitted with a stirrer and thermometer are placed 50.4 parts of 50% cyanamide solution along with 250 parts of water. To this stirred solution, are gradually and simultaneously added 57 parts of methyl chloroformate and 88.2 parts of 50% sodium hydroxide solution. The temperature is maintained at approximately 40° C. during the addition, and the mixture is stirred for an additional half hour.

The resulting slution is acidified to pH 1 with hydrochloric acid and cooled to 20° C. It is then extracted six times with 75 pats of methylene chloride. The combined methylene chloride solutions are dried over 20 parts of anhydrous sodium sulfate and concentrated. The resulting light yellow oil consists essentially of methyl cyanocarbamate.

EXAMPLE 4

Preparaion of 2-benzimidazolecarbamic acid, methyl ester

To a jacketed reactor equipped with feed ports stirrer, reflux condenser, and pH probe are added 32 parts of 50% cyanamide solution and 100 parts of water. Methyl chloroformate (41.1 parts) and 67 parts of 50% sodium hydroxide solution are changed concurrently so as to maintan the pH of the solution at 7 – 7.5 and the reacton temperature at 40° – 50° C. The solution is held at 50° C. for 45 minutes and then 36 parts of o-phenylenediamine is added. The pH of the solution is held at 3.9 to 4.1 by the gradual addition of 65 parts of 37% HCl. The solution is heated to 105° C. and held at this temperature for 30 minutes. During this hold time, the product starts to crystallize. The reaction mass is cooled to 25°–30° C. and the solid product is filtered, washed with water and acetone, and dried in the vacuum oven at 80° C. to give 59.6 parts of 2-benzimidazolecarbamic acid, methyl ester. This represents a product yield of 93.5% based on o-phenylenediamine.

EXAMPLE 5

Preparation of 2-Benzimidazolecarbamic Acid, Methyl Ester

Methyl chloroformate (47.3 parts) and triethylamine (98.8 parts) are added simultaneously to a solution of 21.0 parts of cyanamide in 321 parts of water. The separate addition rates are controlled so that the pH remains between 6.8 and 7.8. External cooling is used to keep the temperature below 55° C.

To this solution is added 45.0 pats of o-phenylenediamine and enough concentrated hydrochloric acid to bring the pH to 4.0. The resulting reaction mass is then heated at 95° – 102° C. for 80 minutes. Concentrated hydrochloric acid is added as needed to maintain a pH of 4.0. The reaction mass is cooled and filtered. The product is washed with water and dried at 100° C. in a vacuum oven. This procedure gives 64.1 parts of 2-benzimidazolecarbamic acid, methyl ester, 80.3% yield based on o-phenylenediamine.

EXAMPLE 6

Preparation of 2-Benzimidazolecarbamic Acid, Methyl Ester

Methyl chloroformate (27.8 parts) is added to a cold solution of 23.7 parts of 50% cyanamide and 100 parts of water. Then 513 parts of a 10% tetramethylammonium hydroxide in water solution is added slowly. External cooling is used to keep the temperature at or below 40° C.

To the product solution is added 25.4 parts of o-phenylenediamine and enough concentrated hydrochloric acid to give a pH of 4.0. The rection mass is then heated at 95° – 100° C. for 3 hours while the pH is kept at 4.0 by the intermittent addition of concentrated hydrochloric acid. The reaction mass is cooled and filtered. The product is washed with water and acetone and dried in a vacuum oven at 100° C. This procedure gives 32.6 parts of 2-benzimidazolecarbamic acid, methyl ester, 72.4% yield based on o-phenylenediamine.

EXAMPLE 7

Preparation of 2-Benzimidazolecarbamic Acid, Methyl Ester

Methyl chloroformate (94.5 parts) and triethanolamine (299 parts) are added simultaneously to a solution of 84.0 parts of 50% cyanamide in 500 parts of water. The separate addition rates are controlled so that the pH remains between 6.2 and 8.0. External cooling is used to keep the temperature below 50° C.

To this reacton mass is added 90.0 parts of o-phenylenediamine and enough concentrated hydrochloric acid to give a pH of 4.0. The reaction mass is then heated at 94° – 10° C. for 2 hours while concentrated hydrochloric acid is added as required to maintain the pH at 4.0. The reaction mass is cooled and filtered. The product is washed with waer and dried at 100° C. in a vacuum oven. This procedure gives 118 parts of 2-benzimidazolecarbamic acid, methyl ester, 74.0% yield based on o-phenylenediamine.

EXAMPLE 8

Preparation of the Sodium Salt of Methyl Cyanocarbamate

Methyl chloroformate (142 parts) and 50% sodium hydroxide (236 parts) are added simultaneously to a solution of 63 parts of cyanamide in 263 parts of water. The separate addition rates are controlled so that the pH remains between 6.1 and 7.6. External cooling is used to keep the temperature below 48° C. The reaction mass is cooled to 4° C. and filtered. The filter cake is washed with a little ice water and dried for 16 hours in a vacuum oven at 95° C.

This procedure yields 131 parts (71.6% yield) of the sodium salt of methyl cyanocarbamate, m.p. 238° C. (with decomposition.) The infrared spectrum (KBr pellet) shows a strong band at 4.55 microns, which is characteristic of the salts of methyl cyanocarbamate.

EXAMPLE 9

Preparation of the Calcium Salt of Methyl Cyanocarbamate

Methyl chloroformate (142 parts) and solid calcium hydroxide (115 parts) are added simultaneously to a solution of 63 parts of cyanamide and 263 parts of water. The separate addition rates are controlled so that the pH remains between 6.0 and 8.0. The temperature is kept below 55° C. by external cooling. The powder funnel used for calcium hydroxide addition is rinsed down with 100 parts of water. The reaction mass is cooled to 0° C. and filtered. The collected solids are dried for 17 hours in a vacuum oven at 95° C.

This procedure yields 41 parts (23% yield) of the calcium salt of methyl cyanocarbamate, m.p.>400° C. The infrared spectrum (KBr pellet) shows a strong band near 4.55 microns, which is characteristic of the salts of methyl cyanocarbamate.

EXAMPLE 10

Preparation of the Potassium Salt of Methyl Cyanocarbamate

Methyl chloroformate (57 parts) and 50% sodium hydroxide (88.2 parts) are added gradually and simultaneously to a solution of 50.4 parts of 50% cyanamide solution and 250 parts of water. The temperature is kept near 40° C. by external cooling. The resulting solution is acidified to pH 1.0 with concentrated hydrochloric acid and cooled to 20° C. It is then extracted with methylene chloride (6 × 75 parts). The extract is dried over anhydrous sodium sulate and concentrated under reduced pressure.

The resulting light yellow oil is taken up in 85 parts of methanol. To this solution is added with cooling a solution of 28 parts of potassium methoxide in 100 parts of methanol. The potassium salt of methyl cyanocarbamate precipitates and is recovered by filtration; it exhibits a m.p. of 212° – 217° C. (with decomposition.) The infrared spectrum (KBr pellet) shows a strong band near 4.55 microns, hich is characteristic of the salts of methyl cyanocarbamate.

EXAMPLE 11

Preparation of Trimethylamine Salt of Methyl Cyanocarbamate

Methyl chloroformate (34.4 parts) and 50% potassium hydroxide (82.0 parts) are added simultaneously to a solution of 15.3 parts of cyanamide in 63.7 parts of water. The separate addition rates are controlled so that the pH remains between 6.4 and 7.6. The temperature is kept below 60° C. by external cooling. The solution is cooled to room temperature and acidified to pH 1.9 with concentrated hydrochloric acid. The solution is then extracted with chloroform (7 × 75 parts). The extract is dried over anhydrous magnesium sulfate and evaporated under reduced pressure.

The residue is taken up in 107 parts of ether. Trimethylamine is then sparged into the ether solution while it is cooled in an ice bath. Sparging is continued until neutralization is complete as evidenced by a rapid temperature drop from 15° C. Filtration and washing with ether give 12.1 parts (21% yield) of the trimethylamine salt of methyl cyanocarbamate, m.p. 57°–62° C. The infrared spectrum (KBr pellet) shows a strong band near 4.55 microns, which is characteristic of the salts of methyl cyanocarbamate.

EXAMPLE 12

The following products are prepared by the procedure of Example 1. The starting materials used and the products obtained in this Example are listed in the following table. The amounts of starting materials are equivalent on a molecular basis to those of Example 1.

TABLE

| STARTING MATERIALS | | | |
|---|---|---|---|
| Cyanamide Salt | Alkyl Chloroformate | o-phenylene-diamine | PRODUCT |
| sodium cyanamide | methyl chloroformate | 3-methyl-o-phenylene-diamine | 4-methyl-2-benzimidazolecarbamic acid, methyl ester |
| potassium cyanamide | propyl chloroformate | 3-chloro-o-phenylene-diamine | 4-chloro-2-benzimidazolecarbamic acid, propyl ester |
| calcium cyanamide | isopropyl chloroformate | o-phenylene-diamine | 2-benzimidazolecarbamic acid, iso-propyl ester |
| calcium cyanamide | ethyl chloroformate | 4-bromo-o-phenylene-diamine | 5-bromo-2-benzimidazolecarbamic acid, ethyl ester |
| magnesium cyanamide | isobutyl chloroformate | 3-nitro-o-phenylene-diamine | 4-nitro-2-benzimidazolcabamic acid, iso-butyl ester |

EXAMPLE 13

Preparation of 2-benzimidazolecarbamic acid, ether ester

To a jacketed reactor fitted with feed ports, stirrer, reflux condenser, bleed off and injector pumps, and pH probe are added 32 parts of 50% cyanamide solution and 100 parts of water. To this stirred solution are concurrently added 47.5 parts of ethyl chloroformate and 67 parts of 50% sodium hydroxide solution. The pH is maintained at 7 – 7.5, and the reaction temperature at 40° – 50° C. The solution is stirred for an additional 45 minutes at 50° C.

To the resulting solution containing the intermediate ethyl cyanocarbamate, sodium salt is added 36 parts of o- phenylenediamine. The vessel is sealed to withstand pressure of the order of 2 – 3 atmospheres. A total of 65 parts of 37% hydrochloric acid is gradually pumped in to maintain the pH at 3.9 to 4.1 while the solution is heated and then held at 130° C. for 20 minutes. The reaction mixture is cooled to ambient temperature, filtered, and the solid washed first with water, then with acetone. The filter cake is dried in a vacuum oven at 80° C. and represents an excellent yield of 2-benzimidazolecarbamic acid, ethyl ester.

EXAMPLE 14

Preparation of 2-Benzimidazolecarbamic Acid, Methyl Ester

Methyl chloroformate (65 parts) and 50% sodium hydroxide (98 parts) are added simultaneously to a solution of 56 parts of 50% cyanamide in 120 parts of methanol. The separate addition rates are controlled so that the pH remains between 6.3 and 7.2. External cooling is provided so that the temperature remains between 38° and 51° C.

To the resulting reaction mass is added 61.2 parts of o-phenylenediamine. A gas inlet tube is then provided for the flask and the mixture is sparged with anhydrous hydrogen bromide until the pH is lowered to 4.3. The reaction mass is then heated at 70°–80° C. for 3 hours while the pH is maintained in the range of 4.0 to 4.8 by intermittent sparging with anhydrous hydrogen bromide. A total of 100 parts of hydrogen bromide are used.

The reaction mass is cooled and filtered. The product is washed liberally with water and finally with methanol. Drying in a vacuum oven at 100° C. gives 86.1 parts of 2-benzimidazolecarbamic acid, methyl ester, a yield of 79.4% based on o-phenylenediamine.

EXAMPLE 15

Preparation of 2-Benzimidazolecarbamic Acid, Methyl Ester

Methyl chloroformate (142 parts) is added slowly to 64 parts of sodium hydrogen cyanamide in 400 parts of methanol. The temperature is kept at 40° to 50° C. during the addition by external cooling.

Next 81.3 parts of o-phenylenediamine is added. Anhydrous hydrogen chloride (27 parts) is sparged in rapidly, then the reaction mass is stirred and heated at 60° C. for 3 hours while another 27 parts of anhydrous hydrogen chloride is sparged slowly into the reaction mass.

The reaction mass is cooled and filtered. The product is washed thoroughly with water and dried in a vacuum oven at 100° C. This procedure gives 93 parts of 2-benzimidazolecarbamic acid, methyl ester. This represents a yield of 65% based on o-phenylenediamine.

A second type of novel compound, the salt of an alkyl cyanocarbamate with o-phenylenediamine or a substituted o-phenylenediamine, is formed during the operation of step 2 of the process of the invention. A convenient way to begin the operation of step 2 is to add the o-phenylenediamine or the substituted o-phenylenediamine to the solution of the alkali metal or alkaline earth metal salt of alkyl cyanocarbamate which is produced in step 1. The resulting mixture is then acidified to the proper pH with a suitable acid. At this point the novel salts are formed. These reactions are represented by the following equation:

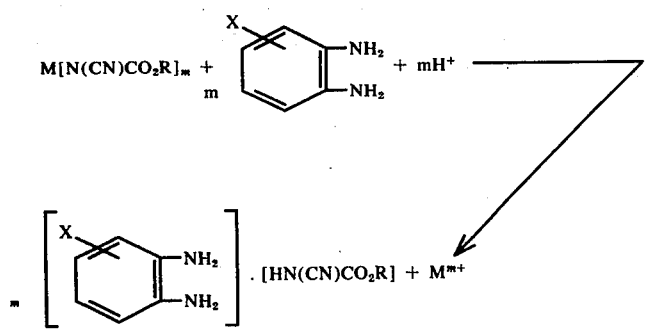

wherein
R is alkyl of 1 through 4 carbon atoms;
X is hydrogen, halogen, nitro or alkyl of 1 through 4 carbon atoms;
M is an alkali metal or alkaline earth metal;
m is the valence of M; and
H⁺ is derived from any acid.

The novel salts of this aspect of the invention can be recovered by conventional methods such as filtration, centrifugation, or spray drying. However, if it is desirable to prepare substituted and unsubstituted esters of 2-benzimidazolecarbamic acid, then it is ordinarily more convenient to proceed with step 2 without isolating the salts. When the novel salts are heated in an acidic medium, as is the case during step 2, they are converted to substituted and unsubstituted esters of 2-benzimidazolecarbamic acid. This reaction is represented by the following equation:

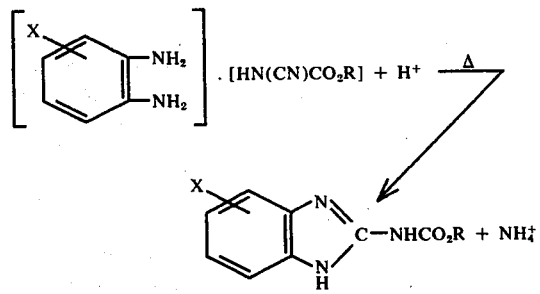

wherein R, X and H⁺ are as previously set forth.

Their ability to eliminate $NH_3$ and form benzimidazolecarbamic acid esters is characteristic of these novel salts and this property can manifest itself under other conditions than those ordinarily employed in the operation of step 2.

For example, although higher yields are obtained when the $NH_3$ is neutralized by added acid, the reaction will proceed in the absence of any additional acid. Also, although the reaction is much more rapid at an elevated temperature, it will occur to an appreciable extent at room temperature. Thus, an aqueous solution of the salt of methyl cyanocarbamate with o-phenylenediamine will deposit solid 2-benzimidazolecarbamic acid, methyl ester, after standing overnight at room temperature. These conversions will also occur in other solvents, such as acetone and the lower alcohols, in which the salts are soluble.

It is not necessary to have the salts in solution; simple dry heating is all that is required to effect this characteristic reaction. For example, when a small sample of the salt of methyl cyanocarbamate and o-phenylenediamine is placed in a melting point bath which is at 125° C., the sample immediately melts with $NH_3$ evolution and then rapidly resolidifies. This dry conversion can be controlled on a larger scale by having the salt suspended in an inert solvent and heating the slurry until the conversion is complete.

Besides their formation during step 2 of the process, these salts can be prepared by other methods. Essentially, the salts are formed whenever an alkyl cyanocarbamate and substituted or unsubstituted o-phenylenediamine are brought together. If they are brought together in a solvent in which the salt is insoluble or only partially soluble, then the salt can be recovered by conventional methods such as filtration, centrifugation, or spray drying.

Thus an aqueous solution of the alkali metal or alkaline earth metal salt of the alkyl cyanocarbamate which is produced in step 1 can be acidified. The alkyl cyanocarbamate can then be extracted by a water-immiscible solvent such as ether, methylene chloride, chloroform, or any of several others. The addition of the substituted or unsubstituted o-phenylenediamine to the extract results in salt formation.

Alternatively, the alkyl cyanocarbamate could be obtained in an undiluted form by evaporation of the extract, and then added to a mixture of the substituted or unsubstituted o-phenylenediamine and the appropriate solvent.

Another method of obtaining these salts involves one of the previously mentioned optional variations of step 2. In this case, a mineral acid salt of the substituted or unsubstituted o-phenylenediamine is added to the product solution of step 1 which contains the alkali metal or alkaline earth metal salt of the alkyl cyanocarbamate. A metathetic reaction takes place and the salt of the alkyl cyanocarbamate with the substituted or unsubstituted o-phenylenediamine will precipitate as a result.

The alkyl cyanocarbamate need not even be preformed; it may be produced in situ. This occurs when a dialkyl cyanoiminodicarboxylate is reacted with a substituted or unsubstituted o-phenylenediamine. The initial products of this reaction are an alkyl cyanocarbamate and the diester of a substituted or unsubstituted o-phenylenedicarbamic acid. The alkyl cyanocarbamate then reacts with additional diamine to form the salt. These reactions are represented by the following equations:

Reaction 1

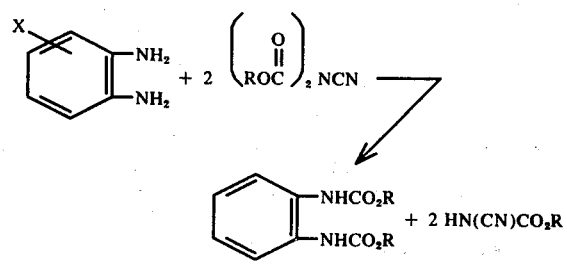

Reaction 2

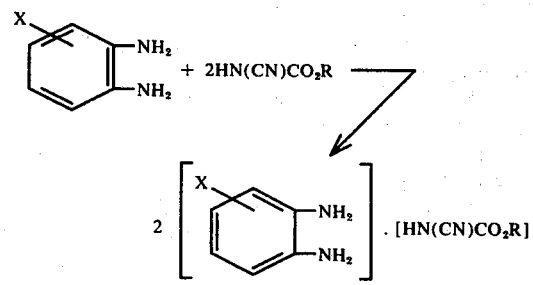

where R and X are as previously defined.

In any of the methods for producing the novel salts, the molar proportions of the alkyl cyanocarbamate and substituted or unsubstituted o-phenylenediamine are not critical variables and either may be in excess when the two are brought together for salt formation. It is obviously uneconomical of material, however, to have one present in great excess over the other.

Temperature is not a critical variable and the salts can be obtained at any temperature below that at which decomposition begins. This temperature will of course vary depending upon the particular salt but decomposition is slow below 50° C. in all cases. A convenient working temperature range for the preparation of these salts is 0° C. to 50° C.

Another characteristic of these salts is their acidity. For example, an aqueous solution of the salt of methyl cyanocarbamate with o-phenylenediamine may be titrated to a sharp end point using 0.1 N NaOH and phenolphthalein indicator.

Application of the novel salts of this aspect of the invention by the followng methods surprisingly entirely precludes or reduces damage to plants due to fungi. Fungus mycelia are killed or prevented from developing further by the presence of one or more of these salts, i.e., the compounds are fungicidal or fungistatic.

These salts provide protection from damage caused by fungi when applied to the proper locus at a sufficient rate to exert the desired fungicidal effect. They are especially suited for the protection of living plants such as fruit-bearing trees and vegetable crops.

Living plants may be protected from fungi by applying one or more of the salts to the soil in which they are growing or in which they may subsequently be seeded or planted at preferred rates of 0.1 to 1000 parts per million by weight of the soil; or to seeds, tubers, bulbs or other plant reproductive parts prior to planting at preferred rates of 0.5 to 4000 grams active compound per 50 kilograms of plant parts treated; as well as to foliage, stems and fruit of the living plant at preferred rates of 0.1 to 100 kilograms of active ingredient per hectare. Living plants can also be protected by dipping the root system or physically injecting the chemical or chemicals into roots or stems. The preferred rates for this utility are 50 to 500 grams per 400 liters of water or other liquid carrier.

Applications are made from dusts, slurries or solutions. Such treatments protect the treated parts themselves from damage due to fungi and, in addition, impart extended protection to the resulting new plants.

Plant parts such as fruits, tubers, bulbs, roots and the like, harvested for food or feed, are protected from decay and other deterioration caused by fungi during processing, distribution and storage by treatment with an active salt of this invention.

As was previously set forth, the salts are especially suited for use in living plants. Application to the foliage, stems and fruit of plants at the rate indicated above is generally accomplished by employing sprays, dusts or aerosols containing an effective amount of active ingredient. For the control of fungi which are regularly present, applications often start prior to the time that the problem actually appears and continue on a pre-determined schedule.

The salts can be formulated into fungicidal compositions which contain in sufficient amount to exert fungicidal action, one or more salts in admixture with a carrier material or conditioning agent of the kind used and commonly referred to in the art as an adjuvant or modifier. The general classes of adjuvants applicable to the salts are inert solids, organic liquid solvents, organic liquid or aqueous diluents and surface-active agents. Formulations adapted for ready and efficient application using conventional applicator equipment are prepared by compounding the salts with suitable adjuvants by mixing, grinding, stirring or other conventional processes. Normally, the active ingredient composes 1 – 95% by weight of the fungicidal composition.

Practical compositions of the salts are wettable powders, dusts or granules. The salts of this invention are sufficiently water soluble to form solutions at normal spray concentrations. However, water solubility is no assurance of rapid wetting and dispersion into water prior to solution. In order that this take place rapidly, without slow-dissolving agglomerates, it is desirable to incorporate an inert diluent to prevent lumping and agglomeration, a wetting agent to prevent surface float and a dispersant to aid dispersion into individual particles so that solution is rapid.

Other compositions are concentrated solutions in water or in a water-miscible solvent such as methanol or acetone, which can be sprayed directly or diluted for application.

Suitable wetting and dispersing agents may be anionic or nonionic. Cationic agents are undesirable since they usually produce low pH mixtures which accelerates product decomposition. A listing of wetting and dispersing agents may be found in "Detergents and Emulsifiers" by John W. McCutcheon, Inc. 1967.

Most suitable wetting agents include alkyl naphthalene and alkyl benzene sulfonates, sodium salts of dialkyl sulfosuccinates, sodium lauryl sulfate, aliphatic sulfonates, the oleyl ester of sodium isethionate and sodium-N-methyl-N-palmitoyl taurate. Liquid nonionic agents such as alkyl phenol polyethyleneoxide condensation products are effective wetting agents but may tend to promote caking or agglomeration in storage because of their physical form. They are best used when preextended upon a high surface area diluent. One commercial product offered in this form is "Triton" X120.

Most suitable dispersing agents are ligninsulfonates, polymerized alkyl naphthalene sulfonate condensates, and protective colloids such as methylcellulose or low viscosity polyvinyl alcohol. Suitable diluents for wettable powders include natural kaolin, attapulgite montmorillonite and diatomaceous silica. Since acidity is undesirable, acidic diluents such as kaolin should be buffered, i.e., with $Na_2HPO_4$, if used. In addition to natural minerals, synthetic products such as calcium silicates and synthetic fine silicas are satisfactory. Diluents for dusts should be dense and rapid settling. Suitable dust diluents include micaceous talcs, pyrophillite, ground phosphate rock and tobacco stem dust. Granular diluents are preferably preformed, screened grades of attapulgite, vermiculite or ground corn cob.

Surface active agents may be added to wettable powders in concentrations of from 0.0% to 2.5% when the objective is merely to attain rapid wetting, dispersion and solution of the active. However, some wetting agents, e.g. sodium lauryl sulfate, have also been found to aid the biological action when used at high levels. Such wetting agents can make up 50 to 90% of the dry composition when a single composition of maximum activity is desired. Dispersing agents do not display this effect and are used only at the lower levels of 0.0 – 2.5%.

Many liquid non-ionic wetters and emulsifiers also enhance biological activity when present at 100 – 1000 ppm in the final spray. Such agents are most conveniently added to the spray tank as a separate component.

In order that this aspect of the invention can be better understood, the following Examples are offered; the parts in all of the Examples are parts by weight unless otherwise indicated.

EXAMPLE 16

Preparation of the Salt of Methyl Cyanocarbamate with o-Phenylenediamine

Separate solutions of 96.0 parts of 50% sodium hydroxide and 65.0 parts of 87% methyl chloroformate are added simultaneously to a solution of 25.2 parts of cyanamide in 100 parts of water. The separate addition rates are controlled so that the pH remains between 6.0 and 7.5. External cooling is used to keep the temperature below 55° C.

Water (100 parts) is added followed by enough concentrated hydrochloric acid (29.4 parts) to give a pH of 3.0. The solution is cooled to 25° C. and 21.6 parts of o-phenylenediamine are added. The resulting slurry is cooled to 10° C. and filtered. The product is washed with cold water and dried at room temperature. This procedure gives 33.8 parts (81% yield) of the salt of methyl cyanocarbamate with o-phenylenediamine.

When placed in a 125° C. melting point bath, a small sample of this salt immediately melts with accompanying $NH_3$ evolution and then rapidly resolidifies.

EXAMPLE 17

Preparation of the Salt of Methyl Cyanocarbamate with 4-Methyl-o-phenylenediamine Separate solutions of 96.0 parts of 50% sodium hydroxide and 65.0 parts of 87% methyl chloroformate are added simultaneously to a solution of 25.2 parts of cyanamide in 250 parts of water. The separate addition rates are controlled so that the pH remains between 6.5 and 8.5. External cooling is used to keep the temperature under 50° C. The solution is cooled to 15° C. and acidified to pH 1.7 with concentrated HCl. The solution is then extracted with ether (6 × 36 parts). Magnesium sulfate is used to dry the combined extract.

A portion (36 parts) of this extract is added to a solution of 12.0 parts of 4-methyl-o-phenylenediamine in 71 parts of ether. A second, oily appearing layer forms immediately. After standing several days the oil solidifies. The product is recovered by filtration, washed with ether, and dried at room temperature. This procedure gives 15.4 parts (70% yield) of the salt of methyl cyanocarbamate with 4-methyl-o-phenylenediamine.

A small sample of this salt partially melts with accompanying $NH_3$ evolution and then rapidly resolidifies when it is placed in a melting point bath which is at 155° C.

EXAMPLE 18

Preparation of the Salt of Methyl Cyanocarbamate with o-Phenylenediamine

Dimethyl cyanoiminodicarboxylate (15.8 parts) and o-phenylenediamine (21.6 parts) are added to 214 parts of ether. The resulting slurry is stirred for an hour at room temperature and is then filtered. The product is washed with ether and dried at room temperature. This procedure gives 18.7 parts (90% yield) of the salt of methyl cyanocarbamate with o-phenylenediamine.

A small sample of this salt immediately melts with accompanying $NH_3$ evolution when it is placed in a melting point bath which is at 125° C. Titration of a larger sample in aqueous solution using 0.1 N NaOH and phenolphthalein indicator gives a neutral equivalent of 211. The theoretical value for the named salt is 208.

The following novel salts can be prepared by any of the procedures described in Examples 16 through 18.

| Salt Name | Salt Structure | |
|---|---|---|
| Salt of Propyl Cyanocarbamate with 3-Chloro-o-phenylenediamine | 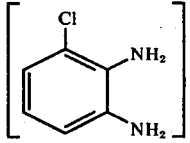 | . [HN(CN)CO₂CH₂CH₂CH₃] |
| Salt of Ethyl Cyanocarbamate with 4-Bromo-o-phenylenediamine | 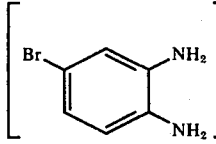 | . [HN(CN)CO₂CH₂CH₃] |
| Salt of Isobutyl Cyanocarbamate with 3-Nitro-o-phenylenediamine | 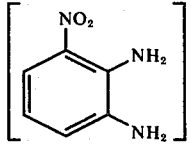 | . [HN(CN)CO₂CH₂CH(CH₃)₂] |
| Salt of Isopropyl Cyanocarbamate with 4-Ethyl-o-phenylenediamine | 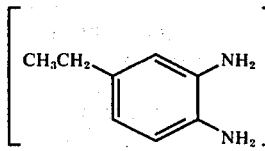 | . [HN(CN)CO₂CH(CH₃)₂] |

| Salt Name | Salt Structure |
|---|---|
| Salt of Butyl Cyanocarbamate with 4-Isopropyl-o-phenylenediamine | $\left[ (CH_3)_2CH\text{-}C_6H_3(NH_2)_2 \right] \cdot [HN(CN)CO_2(CH_2)_3CH_3]$ |
| Salt of Methyl Cyanocarbamate with 3-Butyl-o-phenylenediamine | $\left[ (CH_2)_3CH_3\text{-}C_6H_3(NH_2)_2 \right] \cdot [HN(CN)CO_2CH_3]$ |
| Salt of Methyl Cyanocarbamate with 3-methyl-o-phenylenediamine | $\left[ CH_3\text{-}C_6H_3(NH_2)_2 \right] \cdot [HN(CN)CO_2CH_3]$ |

EXAMPLE 19

Conversion of the Salt of Methyl Cyanocarbamate with o-Phenylenediamine to 2-Benzimidazolecarbamic Acid, Methyl Ester With Heat The salt of methyl cyanocarbamate with o-phenylenediamine (1.0 parts) is heated at 145°–50° C. for 10 minutes. This treatment gives 0.86 parts (94% yield) of 2-benzimidazolecarbamic acid, methyl ester.

EXAMPLE 20

Conversion of the Salt of Methyl cyanocarbamate with o-phenylenediamine to 2-Benzimidazolecarbamic Acid, Methyl Ester with Acid A solution of 5.0 parts of the salt of methyl cyanocarbamate with o-phenylenediamine and 1.5 parts of acetic acid in 25 parts of water is refluxed for 30 minutes. The solution is cooled to 50° C. and filtered. The product is washed with water and dried in vacuo at 95° C. This procedure gives 3.3 parts (72% yield) of 2-benzimidazolecarbamic acid, methyl ester.

EXAMPLE 21

| | |
|---|---|
| Salt of methyl cyanocarbamate with o-phenylenediamine | 80% |
| Oleyl ester of sodium isethionate | 1% |
| Diatomaceous silica | 19% |

The above components are mixed and micropulverized. The resulting powder disperses readily when placed in water, followed by solution of the active component.

This formulation is added to water at a rate to provide 800 parts per million by weight of active ingredient in the total slurry and resulting solution. This solution is sprayed on selected apple trees in a commercial orchard. Application procedure is such as to provide uniform coverage of all foliage to the point of liquid run-off. Applications start at the time that the first spring foliage growth appears and continues at weekly intervals until one month prior to the normal harvest date for apples. At the time of harvest, trees that had been treated in this manner have healthy foliage of good color and provide a good yield of high quality fruit. Similar and adjacent trees left unsprayed, on the other hand, have foliage showing disease caused by the fungi *Venturia insequalis* (scab fungus) and *Podosphaera laucotricha* (powdery mildew fungus). The foliage on the unsprayed trees is also of poor color. The unsprayed trees yield only a few small fruit with diseased spots caused by the fungus *Venturia inaequalis*. Thus, the compound of this invention applied by the method described here effectively prevents damage to crop plants caused by certain fungi.

EXAMPLE 22

| | |
|---|---|
| Salt of methyl cyanocarbamate with 4-methyl-o-phenylene diamine | 25% |
| Tech 92% sodium lauryl sulfate | 75% |

The above components are mixed and micropulverized. When added to water at use concentrations, the product is completely soluble. The high surfactant level enhances the activity of the active compound.

This formulation is added to water at a rate to provide 1,000 parts per million by weight of active ingredient in the final solution. This solution is sprayed on alternate rows of grape vines in a vineyard at the rate of 800 liters per hectare. Such applications start with the earliest growth in the spring and continue at intervals of 12 to 14 days until harvest time.

At harvest time the foliage on the treated vines is healthy and dark green in color and the yield of marketable fruit is high. The alternate unsprayed grape rows have foliage heavily diseased with powdery mildew (caused by the fungus *Uncinula mecator*). Thus, the compound of this invention applied by the method described effectively controls powdery mildew.

EXAMPLE 23

| | |
|---|---|
| Salt of methyl cyanocarbamate with o-phenylenediamine | 10% |

| | |
|---|---|
| -continued | |
| Micaceous talc | 90% |

An equal weight mixture of active and talc is first micropulverized. This product is then blended with the balance of the talc in a ribbon blender to yield a fungicidal dust.

The above dust is applied with a hand duster to designated plots within a large cucumber field. Each application is at the rate of 10 kilograms of the formulation per hectare. The first application is made as the plants start to form runners and this is repeated at intervals of 10 to 14 days until the picking period.

At picking time the plants within the treated plots are healthy and yield well. The untreated areas outside the plots, on the other hand, contain only cucumber plants heavily diseased with powdery mildew (caused by the fungus *Erysiphe cichorocearum*).

EXAMPLE 24

| | |
|---|---|
| Salt of ethyl cyanocarbamate with 4-bromo-o-phenylenediamine | 20% |
| 30 60 mish granular attapulgite | 80% |

The active component is first dissolved in acetone, then sprayed upon the attapulgite in a blender. The acetone is then evaporated from the product.

Selected plots in a rice field are dusted with the formulation described above employing a hand dust applicator. Application is at the rate of 5 kilograms of the formulation per hectare. The first application is made when the rice plants are about 10 inches tall and it is repeated at intervals of two weeks until about 14 days prior to harvest.

The rice within the treated plots remains healthy and yields well. The untreated areas outside the test plots, however, are heavily infected with the rice blast fungus (*Piricularia oryzae*) and provide only a negligible yield of low quality grain.

We claim:
1. A process for making a 2-benzimidazolecarbamic acid ester comprising reacting an alkyl cyanocarbamate of the following formula:

HN(CN)CO₂R where
R is alkyl of 1 through 4 carbon atoms; with an o-phenylenediamine of the following formula:

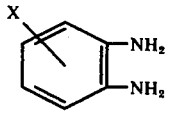

where
X is hydrogen, halogen, nitro or alkyl of 1 through 4 carbon atoms; in the presence of water and sufficient acid to maintain a pH of from 2.5 to 5, until the precipitation of the 2-benzimidazolecarbamic acid ester is complete, and recovering said 2-benzimidazolecarbamic acid ester from the reaction mixture.

2. The process of claim 1 at a temperature from 40° to 130° C.

3. In the process for making a 2-benzimidazolecarbamic acid ester of the formula:

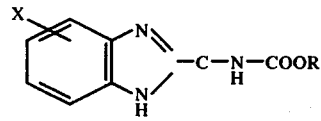

wherein
R is alkyl of 1 through 4 carbon atoms;
X is hydrogen, halogen, nitro or alkyl of 1 through 4 carbon atoms; wherein cyanamide is reacted with an alkyl chloroformate of the formula ClCOOR where R is alkyl of 1 through 4 carbon atoms to form the corresponding alkyl cyanocarbamate salt and said alkyl cyanocarbamate salt is reacted with an o-phenylenediamine of the following formula:

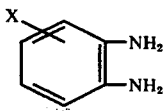

wherein
X is hydrogen, halogen, nitro or alkyl of 1 through 4 carbon atoms; to produce the desired 2-benzimidazolecarbamic acid ester, the improvements comprising reacting the alkyl chloroformate and cyanamide in a weakly acidic to basic medium and reacting the alkyl cyanocarbamate salt and said o-phenylenediamine in the presence of water and sufficient acid to maintain a pH of 2.5 to 5.

4. The process of claim 3 when cyanamide is reacted with the alkyl chloroformate at a temperature between 0° and 105° C. and the alkyl cyanocarbamate salt and o-phenylenediamine are reacted at a temperature of 40° to 130° C.

5. The process of claim 3 wherein the reactants are present in the following mole equivalents:

| | |
|---|---|
| o-phenylenediamine | 1 mole |
| alkyl chloroformate | 1 – 3 moles |
| cyanamide | 1 – 3 moles |

6. A process such as set forth in claim 3 wherein the alkyl cyanocarbamate salt is separated from the reaction mixture prior to being reacted with the o-phenylenediamine.

7. A process for making a 2-benzimidazolecarbamic acid ester comprising reacting an alkyl cyanocarbamate salt of the following formula:

M[N(CN)CO₂R]ₘ where
M is an alkali metal or an alkaline earth metal;
m is the valence of M; and
R is alkyl of 1 through 4 carbon atoms; with an o-phenylenediamine of the following formula:

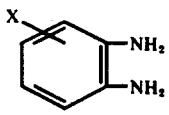

where
X is hydrogen, halogen, nitro or alkyl of 1 through 4 carbon atoms; in an aqueous acidic medium at a pH of 2.5 to 5 until the precipitation of a 2-benzimidazolecarbamic acid ester is complete, and recovering said 2-benzimidazolecarbamic acid ester from the reaction mixture.

8. The process of claim 7 at a temperature from 40° to 130° C.

9. A process for making a 2-benzimidazolecarbamic acid ester comprising reacting an alkyl cyanocarbamate salt of the following formula:

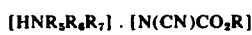

where
$R_5$ and $R_6$ are alkyl of 1 through 4 carbon atoms; and
$R_7$ is alkyl of 1 through 4 carbon atoms, or aralkyl of 7 through 12 carbon atoms;
R is alkyl of 1 through 4 carbon atoms; with an o-phenylenediamine of the following formula:

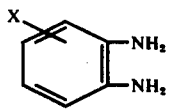

where
X is hydrogen, halogen, nitro or alkyl of 1 through 4 carbon atoms; in an aqueous acidic medium at a pH of 2.5 to 5 until the precipitation of a 2-benzimidazolecarbamic acid ester is complete, and recovering said 2-benzimidazolecarbamic acid ester from the reaction mixture.

10. The process of claim 9 at a temperature from 40° to 130° C.

11. A process for making a 2-benzimidazolecarbamic acid ester comprising reacting an alkyl cyanocarbamate salt of the following formula:

where
$R_1$, $R_2$ and $R_3$ are alkyl of 1 through 4 carbon atoms; and
$R_4$ is alkyl of 1 through 4 carbon atoms or aralkyl of 7 through 12 carbon atoms;
R is alkyl of 1 through 4 carbon atoms; with an o-phenylenediamine of the following formula:

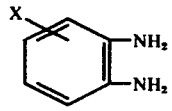

where
X is hydrogen, halogen, nitro or alkyl of 1 through 4 carbon atoms; in an aqueous acidic medium at a pH of 2.5 to 5 until the precipitation of a 2-benzimidazolecarbamic acid ester is complete, and recovering said 2-benzimidazolecarbamic acid ester from the reaction mixture.

12. The process of claim 11 at a temperature from 40° to 130° C.

13. A process for making a 2-benzimidazolecarbamic acid ester comprising reacting an alkyl cyanocarbamate salt of the following formula:

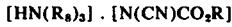

where
$N(R_8)_3$ is triethanolamine or triethylenediamine;
R is alkyl of 1 through 4 carbon atoms; with an o-phenylenediamine of the following formula:

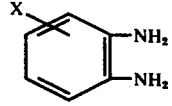

where
X is hydrogen, halogen, nitro or alkyl of 1 through 4 carbon atoms; in an aqueous acidic medium at a pH of 2.5 to 5 until the precipitation of a 2-benzimidazolecarbamic acid ester is complete, and recovering said 2-benzimidazolecarbamic acid ester from the reaction mixture.

14. The process of claim 13 at a temperature from 40° to 130° C.

* * * * *